United States Patent [19]

Leung

[11] Patent Number: 5,039,698

[45] Date of Patent: Aug. 13, 1991

[54] METHOD FOR WEIGHT REDUCTION

[76] Inventor: Lit-Hung Leung, Room 502, Dragon Seed Building, 39 Queen's Road Central, Hong Kong

[21] Appl. No.: 580,445

[22] Filed: Sep. 10, 1990

[30] Foreign Application Priority Data

Oct. 9, 1989 [GB] United Kingdom ............... 8922701

[51] Int. Cl.$^5$ ............................................. A61K 31/355
[52] U.S. Cl. ................................................... 514/458
[58] Field of Search ......................................... 514/458

[56] References Cited

FOREIGN PATENT DOCUMENTS 0129031 12/1984 European Pat. Off. .
0219276 4/1987 European Pat. Off. .
0242554 10/1987 European Pat. Off. .
1381649 1/1975 United Kingdom .

OTHER PUBLICATIONS

Chem. Abst. 66 (1967), 9724G.

Primary Examiner—Stanley J. Friedman
Attorney, Agent, or Firm—Thompson, Hine and Flory

[57] ABSTRACT

A method is described for weight reduction of an individual dieter which comprises administering pantothenic acid or derivative thereof which will generate pantothenic acid in the body in conjunction with a program of reduced caloric consumption.

12 Claims, No Drawings

METHOD FOR WEIGHT REDUCTION

FIELD OF THE INVENTION

This invention relates to a method of weight reduction by using pantothenic acid or derivatives thereof to burn off excess fat in obese people while at the same time alleviating the sensation of hunger and weakness generally experienced by dieters.

BACKGROUND OF THE INVENTION

The battle against obesity has been going on for centuries, with little success. The essence of weight reduction is keeping calorie consumption greater than calorie intake. There have been a great number of methods employed to achieve this goal. The most commonly employed method is by taking a very low calorie diet. However, dieters practicing this method almost invariably run into two problems which will eventually fail their effort. Firstly, dieters will feel very hungry and only those who have very strong will power can stick to their semi-starvation dietary regimen. Others may seek the help of various anorectics. However, the efficacy of these anorectics is limited and their central stimulant effect is also worrying. Their use, if indicated at all, is as an adjunct to dietary control in short term management in moderate to severe obesity and requires close medical supervision. The second and even more tricky situation faced by dieters is the feeling of weakness through lack of calories, and hence lack of energy. In biochemical terms, the dieter are faced with the complications arising from starvation.

During starvation, the body has to derive energy from the stored energy, which includes glycogen and fat. In the first instance, the readily available glycogen store in the body is called upon to supply the energy to maintain life's vital processes. But the glycogen store in the body is very limited, equivalent to about 750 calories' worth of energy. Once it is used up, the fat storage of the body will then be mobilized to supply the energy necessary to sustain life. A portion of the body protein will also be broken down, though the tissues of the body are not treated uniformly, the proteins in the brain and the heart are spared more than the proteins in the muscles, liver and spleen. However, in starvation, by and large, the greatest proportion of energy is supplied by the stored neutral fat in the adipose tissue. This is in contrast to the complex fat, which, forming part of the cell structure, is spared until very late. The use of body fat as the main source of energy brings about the formation of ketone bodies, leading to ketosis. This is a serious condition and has important consequences. The name ketone bodies is applied to three substances (acetoacetic acid, B-hydroxybutyric acid and acetone) which form a metabolically-related group. The ketone bodies are mainly produced in the liver.

The normal blood ketone bodies level in a non-fasting person is small (0.5-2 mg per 100 ml). A short-term fast of two or three days, however, may increase this level by as much as fifty-fold. The amount of ketone bodies in the blood at any time depends upon the balance between ketone bodies formation by the liver (hepatic tissue) and the ketone bodies dissimilation by the extra-hepatic tissue. Little is known about the factors that determine ketone bodies dissimilation. However, there is a maximum amount of fat which the tissues can use (mostly as acetoacetic acid), and this amount has been estimated to be around 2.5 gm of fat per kg body weight per day, or equivalent to 175 gm of fat daily in a 70 kg man. The rate of ketogenesis (the generation of ketone bodies) in the liver varies greatly according to circumstances. If ketogenesis proceeds at a high rate, as in starvation, and exceeds the rate of dissimilation in the extra-hepatic tissues, ketone bodies will begin to accumulate in the blood, and be excreted in the urine. In extreme cases of ketosis, urinary ketone bodies output may reach 100-120 gm per day. Obviously, if the ketone bodies can be broken down and metabolized, a biochemical cure of obesity may be possible. An understanding of the formation of ketone bodies at this point would be helpful. When required, the neutral fat is hydrolyzed, releasing glycerol and long-chain fatty acids, the majority containing 16 or 18 carbon atoms. The next stage is the breakdown, mainly in the liver, of these long carbon chains into fragments containing two carbon atoms each. This breakdown process actually involves the conversion of the fatty acid into its high-energy Co A (Coenzyme A) derivative by reaction of the acid with ATP (Adenosine triphosphate) and Co A. This will produce a Co A ester. This Co A ester eventually will react with another Co A, splitting off a acetyl-Co A (a two carbon fragment), leaving the original long-chain fatty acid with two carbon atoms less, but still as a Co A ester. The whole process can be repeated, splitting off a two carbon fragment each time. Thus a 16 C long-chain fatty acid will yield 8 separate fragments of acetyl-Co A. The conventional idea of the fate of the acetyl-Co A in starvation is supposed to be either of the following:

(a) The acetyl-Co A formed can be completely dissimilated via the citric acid cycle if sufficient oxaloacetic acid is available from elsewhere. Coenzyme A is thus freed for further fatty acid cleavage.

(b) Instead of being oxidized, pairs of acetyl-Co A units can react together to form the four carbon ketone body acetoacetic acid. Initially, this condensation produces free Co A and acetoacetyl-Co A, but the latter is rapidly converted to free acetoacetic acid. The acetoacetic acid is distributed to the tissues, and is there oxidized to carbon dioxide and water, liberating energy in the process. The proportion of acetyl-Co A forming acetoacetic acid rather than being immediately oxidized to carbon dioxide is determined by the availability of oxaloacetic acid from some source, e.g., from pyruvic acid or from aspartic acid.

If the rate of carbohydrate dissimilation is depressed (as in starvation), then the availability of oxaloacetic acid is depressed, and the proportion of acetoacetic acid formed will rise. The exact mechanism whereby the acetoacetic acid is metabolized is not known, but one point is quite certain, the body only has a limited means to metabolize the ketone bodies. If the rate of production of the ketone bodies is increased, they will begin to accumulate in the blood and the condition is known as ketosis. A severe degree of ketosis can make an individual feel very sick, weak, and nauseated. The kidneys will try to get rid of the excess ketones via the urine. however, if the function of the kidneys is stretched beyond its limits, the acidic ketones can build up to dangerous, even toxic, levels in the blood. The high acidity can cause the brain to malfunction, leading to loss of consciousness, or even death.

In view of the foregoing, it is apparent that if there is an agent that will burn off all, or most of the acetoacetic acid produced during starvation, the whole problem of weight reduction through a biochemical means would be achieved. This is the primary aim of modern research on obesity, to achieve weight reduction through a biochemical agent. The problem of ketosis, with its sequelae, would be avoided. At the same time, burning off of the acetoacetic acid would mean a lot of energy release, and the problem of hunger and weakness would be solved simultaneously. Hunger sensation is a topic that is poorly understood, but it is known that if the body is well supplied with energy, the sensation is suppressed. It has been mentioned in the foregoing that the body can handle only a small proportion of the acetoacetic acid produced during starvation, but the metabolism of this small proportion of acetoacetic acid is not well understood. It is generally assumed that the acetoacetic acid is first broken down into two Acetyl-Co A by free Co A, these are then oxidized by the enzymes of the citric acid cycle present in the tissue concerned. But there is still a question as to why the majority of the acetoacetic acid molecules are not broken down and metabolized. The very fact that the pairing of the acetyl-Co A units to form acetoacetyl-Co A, liberating a free Co A in the process, and the rapid conversion of acetoacetyl-Co A into acetoacetic acid, liberating yet another Co A molecule, may mean that the body is really deficient in Co A, and that this is an effort to conserve Co A molecules so that long-chain fatty acid can be fragmented. This deficiency in Co A can be a result of deficiency in pantothenic acid, because the other components of Co A are never in short supply. Pantothenic acid, one of the B group of vitamins, is a component of Co A. Pantothenic acid is commercially available from Legere Pharmaceuticals as Dexol TD tablets. According to *MARTINDALE, the Extra Pharmacopoeia*, 29th edition (1989), pantothenic acid is widely distributed in foods. Meat, legumes, and whole grain cereals are particularly rich sources; other good sources include eggs, milk, vegetables, and fruits. Recommended daily intakes of pantothenic acid have not been set in the U.K. or in the U.S., but human requirements are adequately met by a daily intake of about 4 to 10 mg.

According to Goodman and Gilman's *The Pharmacological Basis of Therapeutics*, 7th edition (1985), pantothenic acid is a required nutrient, but the magnitude of need is not precisely known. Accordingly, the Committee on Dietary Allowances provides provisional amounts in the form of ranges of intakes (in different age groups). For adults, the provisional allowance is 4 to 7 mg per day. Intakes for other groups are proportional to calorie consumption. Thus, infants will require 2-3 mg per day, and children and adolescents, 3-7 mg per day. In view of the wide-spread distribution of pantothenic acid in foods, dietary deficiency is very unlikely.

If an adequate amount of pantothenic acid is present, providing enough Co A, the metabolism of acetoacetic acid can go on breaking up into two molecules of acetyl-Co A, and henceforth going into the citric acid cycle, to be completely metabolized into carbon dioxide and water, with liberation of energy. Or the adequate supply of Co A may render the pairing of acetyl-Co A and the conversion of acetoacetyl-Co A into acetoacetic acid and Co A unnecessary, so that ketone bodies will not be formed at all. By taking in pantothenic acid, a dieter can take in a low calorie diet containing all the essential nutrients. The extra calories required by the body can be supplied from fat in the fat depot. As long as there is excess fat in the body, it can be burned off in this manner. This method will make weight reduction healthy and effective, but with almost no hunger and weakness. It should be noted that with this method, the body exercise that is stressed so much in conventional weight reduction is not required, though extra exercise will help to burn off the body fat faster, making the process of weight reduction even more effective.

The following is a brief account of Pantothenic Acid:

History

Pantothenic acid was first identified by Williams and associates in 1933 as a substance essential for the growth of yeast. See Williams et al., J. Am. Chem. Soc., Vol. 55, p. 2912 (1933). Its name, derived from Greek words signifying "from everywhere," is indicative of the wide distribution of the vitamin in nature. The role of pantothenic acid in animal nutrition was first defined in chicks, in which a deficiency disease characterized by skin lesions was known to be cured by fractions prepared from liver extract. In 1939, Wolley et al. and also Jukes demonstrated that the chick antidermatitic factor was pantothenic acid. See, for example, *J. Am Chem. Soc.*, Vol. 61, pp. 975 and 977 (1939).

Chemistry

Pantothenic acid, (+)-(R)-3-(2,4-Dihydroxy-3,3-dimethylbutyramido)propionic acid, is an optically active organic acid and biological activity is characteristic only of the d isomer. The vitamin functions in the body following its incorporation into Coenzyme A.

Pharmacological Actions

Pantothenic acid has no outstanding pharmacological actions when it is administered to experimental animals or normal man. The vitamin is essentially nontoxic; as much as 10 gm can be given daily to a human without producing symptoms. See Dumm, M. E. and Ralli, E. P., *Metabolism* 2, 153 (1953). According to *MARTINDALE, The Extra Pharmacopoeia* (1989), pantothenic acid is reported to be generally nontoxic.

Physiological Functions

Coenzyme A, the physiological active form of pantothenic acid, serves as a cofactor for a variety of enzyme-catalyzed reactions involving transfer of acetyl (two-carbon) groups; the precursor fragments of various lengths are bound to the sulfhydryl group of coenzyme A. Such reactions are important in the oxidative metabolism of carbohydrates, gluconeogenesis, synthesis and degradation of fatty acids, and the synthesis of sterols, steroid hormones, and porphyrins. See, Wright, L. D., "Pantothenic Acid", *Present Knowledge in Nutrition*, The Nutrition Foundation, Washington, D.C., pp. 26-231 (1976).

Symptoms of Deficiency

Pantothenic acid is essential for the growth of various microorganisms. In experimental animals, deficiency of pantothenic acid is manifested by symptoms of neuromuscular degeneration, adrenocortical insufficiency, and death. Pantothenic acid deficiency has not been recognized in man consuming a normal diet, presumably because of the ubiquitous occurrence of the vitamin in ordinary food. Experimentally-induced deficiency produces intermittent diarrhoea, insomnia, leg cramps, and parasthenia. There is no persuasive evidence that pantothenic acid has therapeutic efficacy.

Absorption, Fate, and Excretion

Pantothenic acid is readily absorbed from the gastrointestinal tract. it is present in all tissues, in concentrations from 2 to 45 micrograms per gram. Pantothenic acid apparently is not metabolized in the human body since the intake and the excretion of the vitamin are approximately equal. About 70% of the absorbed pantothenic acid is excreted unchanged in the urine.

SUMMARY OF THE INVENTION

The present invention relates to the use of pantothenic acid in dieting. In the process, the almost complete combustion of the fatty acids is believed to provide the body with enough energy to alleviate the weakness so often associated with a low calorie diet, and the sensation of hunger. At the same time, the production of ketone bodies is believed to be kept to a minimum, averting all the sequelae of ketosis. The method comprises giving the dieter 0.5 to 2.0 gm of pantothenic acid or derivative thereof orally in the form of capsules, tablets or liquid in 4 or 5 divided doses at about 4-hour intervals, with a total daily intake of approximately 2 to 10 gm of the pantothenic acid. Because of the nontoxic nature of the vitamin, no side effect is experienced. Pantothenic acid is readily soluble in water and therefore can be effectively administered if desired as a aqueous or saline solution via intramuscular or intravenous injection. Typically, the solution for injection contains approximately 10 mg of benzyl alcohol for indolence. Furthermore pantothenic acid may be admixed with a suitable base or carrier such macrogols and administered rectally as a suppository, but oral administration is the more convenient route.

Definitions

The term "pantothenic acid" as used herein is intended to include pantothenic acid or a derivative thereof which generates pantothenic acid in the body to form Coenzyme A.

DETAILED DESCRIPTION OF THE PREFERRED EMBODIMENTS

The purpose of this invention is to achieve weight reduction in people with excess fat in their body without undue discomfort or complications. One can even achieve the goal without exercise, though exercise will help to speed up the process.

In all weight reducing diets, one important issue is to keep the body well supplied with all the essential dietary nutrients, while at the same time reducing the calorie intake. This ensures that the health state of the dieter is not adversely affected. In general, a drastic weight reduction within a short time is not advisable. A loss of one kilogram of body weight per week is well tolerated and, depending on the degree of obesity, more can be tolerated in those whose obesity is excessive. For easy calculation, presume that the loss of body weight is one kilogram per week, and is pure fat, the body would have to have a negative balance of 9000 calories per week But in actual practice, instead of pure fat, the body would also lose a bit of protein, some carbohydrate and some water. So that, with a loss of one kilogram of body weight per week, in terms of calories, the negative balance is in the region of about 7000 calories. This is equivalent to a negative balance of 1000 calories per day. The calories required by an individual depend on a number of factors, and the range can be very large. On the average, a woman will need somewhere in the range of 2000 calories per day, and a man 2700 calories. With a negative balance of 1000 calories per day, a woman can still take in 1000 calories a day, and a man 1700. That is to say that, with the counsel of a dietitian, a dieter can have all the essential nutrients included in the diet, and the health of the dieter will not be affected.

Administration of pantothenic acid in these circumstances serves several useful purposes.

1. The dieter will be hunger-free. In fact, the amount of pantothenic acid administered can be titrated with the amount of calorie intake. With a greater amount of calorie intake, the amount of pantothenic acid required will be smaller. On the other hand, if the calorie intake is small, more pantothenic acid will be required. If the case is taken to the extreme, when there is no calorie intake at all, the dieter can still be hunger-free, provided that the pantothenic acid administered is enough. In such instances, about 8 to 10 gm of the vitamin will be required. While the dieter may lose about 0.3–0.4 kg of body weight per day, this is not the healthiest way to lose weight. Normally, there is a certain amount of wear and tear of the body tissue going on all the time, and replenishment of tissue in these wear and tear processes is always necessary to maintain the body in optimum health. That is why a drastic reduction in body weight is generally not recommended. Under such circumstances replenishment of all the essential dietary requirements is always difficult.

2. Dieters given pantothenic acid not only have the sensation of hunger suppressed, they do not feel weak, either. This is due to the ample supply of energy from the complete breakdown of acetoacetic acid. Actually, the sense of well being is improved. The explanation is not immediately apparent. However, if the strategic position of coenzyme A in the metabolism of fat, carbohydrate and protein is recognized, one may surmise that the functions of pantothenic acid are as yet not entirely known, and the recommended dietary allowance of 4–7 mg per day may be a gross underestimate to keep the body in the optimum state of health. A good supply of pantothenic acid may hence improve the health state of the individual. This speculation is supported by another observation. If the amount of calorie intake is unchanged, the amount of pantothenic acid required to suppress hunger and generate energy will be reduced after a few days and the amount required will remain relatively constant thereafter. This suggests that the body, initially, is not saturated with this vitamin.

3. Pantothenic acid, unlike the anorectics, does not suppress appetite. It is a natural food and functions as a component of coenzyme A. Coenzyme A is a constituent of the body and has no action on the satiety center of the brain. That is why even with a large amount of pantothenic acid administered, a person can still enjoy a good meal, if he chooses to, with no effect whatsoever on the appetite. This contrasts its function as a hunger suppressant, which operates (through fatty acid metabolism of stored body fat) only when there is a deficient calorie intake.

4. With pantothenic acid as an agent to reduce weight, there is no need to restrict water intake. The weight reduction is achieved through the combustion of stored neutral fat, a bona fide anti-obesity agent. This is in contrast to some of the weight reducing agents on the market, which only achieve a quick, and yet temporary effect through diuresis, a process in getting rid of water already present in the body. Under such circumstances, the body will regain its weight once sufficient fluid intake is resumed. Pantothenic acid is quite different in this respect. The body again excretes a lot of urine, even without a lot of water intake. But the urine actually represents the final product of fatty acid metabolism, aside from carbon dioxide. And this is quite different from the water excreted during diuresis, which is not a product of metabolism.

5. Pantothenic acid is a natural substance present in the body, and it is a food. That is why, unlike any synthetic drugs. it has no side effect in the body. As much as 10 gm can be taken in one day without any untoward effect. In actual practice, few dieters will require as much as 10 gm of pantothenic acid a day to stave off the hunger and weakness so often associated with a low calorie diet. In fact, the amount of pantothenic acid required varies considerably with human biochemical individuality.

Linus Pauling, in his work on vitamin C, (*Vitamin C, The Common Cold and the Flu*, W. H. Freeman & Co., San Francisco, p. 80) stressed that the optimum daily intake of vitamin C for most adult human beings lies in the range of 2.3 to 9 gm. The amount of individual biochemical variability is such that for a large population the range may be as great as from 250 mg to 10 gm or more per day, despite the fact that the recommended daily allowance for male adults is but 60 mg. The same argument probably holds true for pantothenic acid. it is interesting to note here that the plasma concentration of vitamin C in people with an adequate intake of 60 mg of vitamin C a day is in the region of 0.5 mg/dl, and the tissue concentration of pantothenic acid which in fact is present in all tissues, is 0.2 to 4.5 mg per 100 gm of tissue. There can be no conclusions drawn from these figures, but it does suggest that the optimum daily requirement for pantothenic acid can be well above 4 to 7 mg, and the pantothenic acid required by dieters taking a low calorie diet can vary through a great range. it has been estimated that the range probably lies between approximately 2 to 10 gm a day, to be taken in 4 to 5 divided doses at about 4-hourly intervals. With this dose of pantothenic acid, and a strict low calorie intake, the dieter can easily achieve a weight reduction of 1 kg a week, without any sensation of hunger and weakness being felt. This process can go on week after week, uninterrupted, until the desired weight is achieved.

One practical aspect about weight reduction is the maintenance of the desired weight after the reduction is achieved. From observation, we know that most people will accumulate fat gradually when they reach their middle age. Over the years, they tend to have a pot-belly, even if their diet does not change. Another common observation is that people seem to vary as to their natural inclination to get fat even if their diet and activity are more or less the same. While it is not easy to explain these phenomena, one possible explanation that relates to the present invention lies in the difference of biochemical variability of pantothenic acid of different individuals. It seems that in reversing the stored fat into energy, a good supply of pantothenic acid is required. And it also seems that pantothenic acid works more efficiently in the young, with the efficacy of the vitamin falling off as the person ages. Another possibility is that there may not be a decrease in efficacy of the vitamin, but rather the absorption of the vitamin is decreased with age. Or both may be true. Nevertheless, when there is a relative deficiency of pantothenic acid in the body, the stored fat is unable to be mobilized easily, which means the body has a tendency to accumulate fat, and the individual tends to put on weight. That is to say, between two individuals whose activity and calorie intake are more or less the same, the one with a better supply of pantothenic acid, or the one with the more efficient use of the vitamin, can stay more slim than the other.

The same reasoning can account for the increase in weight as an individual advances into the middle age. What can be inferred from these observations is that, given a good supply of pantothenic acid in the body, the tendency to get fat will be decreased. This conclusion, in fact, correlates well with clinical experience. A dieter, when the desired weight is achieved, can maintain that weight more easily if a maintenance dose of the vitamin is taken, even at the expense of not strictly adhering to the calorie intake of the maintenance diet. The maintenance dose is estimated to be in the range of 0.5 to 2 grams a day in 4 or 5 divided doses at about 4-hour intervals. This hypothesis is further supported by yet another observation. Simple dieting without resort to any drug, in fact, can be very successful in some individuals. These people may experience a bit of hunger and a little weakness, but if the process is conducted in a slow and steady manner, they can still successfully reduce their weight. They probably represent those who have a better supply of pantothenic acid in their body. Mobilization and metabolism of fat are possible under such circumstances. However, there are certain individuals, whenever the calorie intake is less than the expenditure, who will feel truly hungry and truly weak. It seems that they have lost their power to mobilize their fat store. These cases probably represent a gross deficiency in pantothenic acid, and it is in these cases that administration of the vitamin provides the best results.

During the process of weight reduction with pantothenic acid, it is remarkable to note that the loss of girth from the waist, the hip, the thigh and the arm is not proportional; there is a preferential loss of the waist girth as compared to the hip, the thigh and the arm. That is, the loss of girth is most obvious at the waist, then the hip, then the thigh, and finally the arm.

To explain this observation, the understanding of the factors involved in the moding of the body contour and how these factors are related to pantothenic acid is necessary. Research has shown that the most important single factor involved in the moding of body contour is the group of sex hormones called the estrogens. The estrogens are responsible for the moding of the perfect body contour of a young female, though the exact manner as to how this is executed is poorly understood. The estrogens are also responsible for the changes that take place at puberty in girls, including the growth and development of the vagina, uterus and fallopian tubes. They are also responsible for enlargement of the breasts at puberty. The estrogens are synthesized in the ovary by converting acetate, in the form of acetyl-Co A, to cholestrol and subsequently to other steroids, and ultimately from androstenedione and testosterone, the male hormones, as the immediate precursors. It should now be clear that pantothenic acid, as a component of acetyl-Co A, is closely related to the synthesis of the estrogens as well as the whole lot of steroid compounds, thus affecting their blood levels. As a female advances into her middle age, there is a relative deficiency of pantothenic acid in the body, and it is only logical that the levels of the estrogens will decline, and the body contour will change accordingly with deposition of fat in the abdomen, the hip, the thigh and the arm, in that order, as is generally observed. In fact, the above description also helps to explain why generally the female is the fatter sex than the male, and further supports the proposition that pantothenic acid deficiency will affect the fat distribution in the body.

The following data serve to illustrate this point. Studies relating to the male hormones (also synthesized from acetyl-Co A, as explained above) showed that in the adult male, plasma testosterone concentration ranges from 0.2 to 1 microgram per dl, and the rate of production is 2.0 to 11 mg per day. See Rosenfield, R. L., "Role of Androgens in Growth and Development of the Fetus, Child, and Adolescent", *Adv. Pediatr.*, Vol. 19, pp. 172-213 (1972). However, measurements of the rate of secretion of progesterone, the main bulk of female hormones secreted, showed that, from a few milligrams a day secreted during the follicular phase of the cycle, the rate increases to 10 to 20 mg during the luteal phase and to several hundred milligrams during the latter part of pregnancy. See Vande Wiele, R. L. and Dyrenfurth, I., "Gonadotropin-Steroid Interrelationships", *Pharmacol. Rev.*, Vol. 25, pp. 109-207 (1973). These figures speak very clearly for themselves. Pantothenic acid, in the form of acetyl- Co A, is the building block for the synthesis of these steroid hormones. The more the vitamin is engaged in the sex hormone synthesis, the less will be spared for fatty acid metabolism. Hence, the female, having spent more of the pantothenic acid in synthesizing the female hormones, has less of the vitamin rationed towards fatty acid metabolism and, therefore, has a higher tendency to get fat than the male. This suggests that, in the distribution or rationing of pantothenic acid towards various functions in the body, the synthesis of the sex hormones overrides fat metabolism which explains why women get so fat when they are pregnant. And depending on their biochemical variability, women who have a relatively more liberal supply of pantothenic acid in their body are able to get rid of the extra fat accumulated during pregnancy after delivery, whereas others, having a relatively short supply of the vitamin, are unable to reverse the situation, unless they are prepared to spend a lot of effort on conventional dieting and exercise.

Pantothenic acid, in the form of acetyl- Co A, serves many functions in the body. Some of these functions may not have been recognized by modern medicine as yet. The distribution of the vitamin to perform various duties in the body may pose a problem. Fortunately, in the body, there is a system called the auto-regulation system which will regulate the needs of the body to its optimal state provided that the functioning of the bodily mechanism is not at fault and the supply of raw materials is adequate. This is well illustrated by the balance of male and female hormones in the body. In the human body, be it a male or a female, there is always present the male and female hormones. However, the ratio of the male to female hormones is quite different between the male and the female. That is to say, in the male, the majority of the hormones is testosterone (androgens) and the level of estrogens in the blood is low. In the female, the opposite is true. There is a high level of estrogens and a low level of androgens. The exact ratio of the male and female hormones in the male or female body varies, so that the optimal ratio is difficult to determine, and it probably varies from individual to individual. Provided that the glands secreting these hormones are functioning normally, and there is a good supply of the raw materials, the body will always finely tune the mechanism of auto-regulation to such a degree that the optimal ratio between the two hormones will be reached. So, in the event of a sufficient supply of pantothenic acid in the body, the optimal ratio of the male and female hormones, as well as any other functions that necessitate the participation of acetyl- Co A, will be reached according to the individual needs. However, if the pantothenic acid is in short supply, the ratio of these various functions will be at fault, leading to various clinical presentations, with the abnormal and unsightly distribution of body fat but a part of the clinical picture. However, with a sufficient supply of pantothenic acid, the whole process is reversed, and the body contour tends to revert to the state of the young and attractive female.

EXPERIMENTAL EXAMPLES

About 100 overweight individuals were given pantothenic acid orally in the dosage of 0.5 to 2.0 gm 4 times a day, with a total daily intake of 2 to 8 gm, while the dieters were given a strict diet control of about 1000 to 1200 calories per day. Initially, all the dieters were started with 6 gm of the vitamin a day in four divided doses. The dosage was then readjusted according to the needs of the dieters. All the essential dietary supplements were included in the diet. Dieters were closely monitored, including urine tests and blood tests. Daily changes in the body weight were particularly noted. Measurements of the girth of the waist, the hip, the thigh and the arm were registered. over a period of 6 to 12 weeks, the average weight loss was 1.2 kg per week, with a range of 0.8 to 1.8 kg per week, and a total loss of 7.2 to 14.4 kg. Many of the dieters who were not grossly overweight would have achieved their goal after 4 to 8 weeks with an average total weight loss of 5 kg to 10 kg during that period. For those who were excessively overweight, the regimen was carried on to 12 weeks and beyond, depending on the aim of the dieters. However, the average loss of 1.2 kg could be maintained with little difficulty. Two dieters lost 25 kg in 22 weeks. All these dieters were not only hunger-free, but they could carry on their normal work, and in most instances, the subjective well-being was improved. In a few occasions, the dosage of the pantothenic acid had to be stepped up to 9 gm a day to stave off the hunger sensation, but in some instance, the dosage required was less than 2 gm a day, sometimes even as little as 1 gm a day.

In order to suppress the hunger sensation, sometimes the dosage of the pantothenic acid could be varied according to the diet, with a bigger dosage when a small meal was anticipated, and vice versa for a bigger meal. In fact, with a bigger meal, the pantothenic acid could sometimes be omitted altogether. The urine ketone bodies were constantly checked, and most of the time, a one plus of ketone bodies was about the worst observed, though occasionally, there was a two plus, and very rarely, a three plus of ketone bodies in the urine. In such instances, corrections were made to increase the pantothenic acid intake, or slightly increase the calorie intake. Blood tests were unchanged. The first noticeable change in girth was always the abdomen, the explanation and the relation to estrogen were given earlier. As related to breast development in girls in the puberty as a result of the optimal estrogen levels, little data had been gathered because the age of dieters fell into a different age group. Further studies in the adolescent group will need to be carried out before anything valid can be established.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

What is claimed is:

1. A method for weight reduction of an individual dieter which comprises administering to said dieter a weight-reducing effective amount of pantothenic acid or a derivative thereof which will generate pantothenic acid in the body in conjunction with a program of reduced caloric consumption.

2. The method of claim 1 wherein said pantothenic acid or derivative thereof is administered in a dosage of approximately 2 to 10 grams per day.

3. The method of claim 2 wherein said pantothenic acid or derivative thereof is administered in 4 or 5 divided does.

4. The method of claim 3 wherein said pantothenic acid or derivative thereof is administered orally, intramuscularly, intravenously or rectally.

5. The method of claim 4 wherein said pantothenic acid or derivative thereof is administered orally in the form of a capsule, a tablet or a liquid.

6. The method of claim 5 wherein said pantothenic acid or derivative thereof is administered orally in the form of a capsule.

7. A method for maintaining the body weight of an individual dieter at a relatively constant level after weight reduction of said dieter comprising administering to said dieter a weight-maintaining effective amount of pantothenic acid or a derivative thereof which will generate pantothenic acid in the body.

8. The method of claim 7 wherein said pantothenic acid or derivative thereof is administered in a dosage of approximately 0.5 to 2 grams per day.

9. The method of claim 8 wherein said pantothenic acid or derivative thereof is administered in 4 or 5 divided doses.

10. The method of claim 9 wherein said pantothenic acid or derivative thereof is administered orally, intramuscularly, intravenously or rectally.

11. The method of claim 10 wherein said pantothenic acid or derivative thereof is administered orally in the form of a capsule, tablet or a liquid.

12. The method of claim 11 wherein said pantothenic acid or derivative thereof is administered orally in the form of a capsule.

* * * * *